(12) United States Patent
Stewart et al.

(10) Patent No.: US 6,197,281 B1
(45) Date of Patent: *Mar. 6, 2001

(54) WET APPLIABLE, INSTANT PROTECTION SUNSCREEN AND MAKEUP AND METHOD OF USE

(75) Inventors: Ernest Glading Stewart, Thomasville, GA (US); Kenneth Klein, Fair Lawn, NJ (US)

(73) Assignee: Ernest G. Stewart, Thomasville, GA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/868,766

(22) Filed: Jun. 4, 1997

(51) Int. Cl.⁷ ..................................................... A61K 7/42
(52) U.S. Cl. .............................. 424/59; 424/60; 424/401; 514/506
(58) Field of Search ................................. 424/59, 60, 401; 514/506

(56) References Cited

U.S. PATENT DOCUMENTS 5,152,983 * 10/1992 Nambudiry et al. .................... 424/60
5,216,033 *  6/1993 Pereira et al. ......................... 514/884

* cited by examiner

Primary Examiner—Shelley A. Dodson
Assistant Examiner—Michael A. Williamson
(74) Attorney, Agent, or Firm—Sanford J. Asman

(57) ABSTRACT

The sunscreen or makeup may be applied to a person who is wet, or even underwater, yet it will provide the fill efficacy which it would have had had it been applied to the person when their skin was dry. In addition, it will be effective from the time that it is first applied, so no waiting period is required, as was the case for the so-called "water resistant" and "waterproof" sunscreens of the prior art.

A series of test procedures which illustrate the efficacy of the "wet-appliable" sunscreens of the present invention are disclosed.

44 Claims, No Drawings

WET APPLIABLE, INSTANT PROTECTION SUNSCREEN AND MAKEUP AND METHOD OF USE

BACKGROUND OF THE INVENTION

The present invention relates to sunscreens. In particular, the present invention relates to sunscreens which can be applied to a person whose skin is wet or dry and which achieves its fill SPF instantly, irrespective of whether it was applied to wet or dry skin. The invention further relates to inventive procedures for testing the effectiveness of sunscreens.

In recent years, the dangers of exposing the skin to direct sunlight have become known. Consequently, the concept of having a "healthy" tan has changed to one of protecting the skin from the harmful effects caused by exposure, particularly to the ultraviolet ("UV") rays of the sun, which have been shown to cause many skin problems, including cancers, such as melanoma. These effects have been shown to be cumulative over a person's life, and no way has been found to reverse these effects.

Accordingly, modern thinking involves not exposing one's skin to the direct rays of the sun unless the skin is either covered or otherwise protected. Numerous sun screen products are available to protect the skin from the harmfull rays of the sun. These sunscreen products are rated based upon their ability to protect the user's skin, using a rating system which is based upon a Sun Protection Factor ("SPF") rating. The higher the SPF of a sunscreen, the greater the amount of protection which the sunscreen provides to a user.

Among the various sunscreens which are available are a number which are called either "water resistant" or "waterproof". What consumers do not generally recognize, however, is that such sunscreens are only water resistant or waterproof after they have been applied to the user, and after they have been allowed to dry, whereby they are, themselves, protected from water by a thin film. In accordance with the instructions and test procedures used with such so-called "water resistant" and "waterproof" sunscreens of the prior art and generally not known by, or, alternatively, disregarded by, consumers, is that the sunscreens must be applied to the dry skin of a user in order for them to have the SPF which they claim to have. In fact, the very test procedures heretofore used to test the efficacy of sunscreens requires that the sunscreens be applied only to dry skin.

The so-called "water resistant" and "waterproof" sunscreens of the prior art, must all be applied to dry skin, then allowed to dry on the user's skin for a period of time, typically twenty minutes, before they are effective. In fact, while no rules have been adopted by the federal Food and Drug Administration ("FDA"), the industry has operated pursuant to the proposed rules which were published on May 12, 1993 in Volume 58, No. 90 of the Federal Register, which require a waiting period of at least 15 minutes before exposure prior to testing the SPF of a sunscreen. Similarly, the proposed rules also set forth a methodology for determining the water resistance of a sunscreen product. In accordance with the water resistance testing, a determination is made as to whether a sunscreen is able to retain the same Product Category Designation ("PCD"). As is known by those skilled in the art, the PCD of a sunscreen is based upon its SPF value, as follows: "minimal" means the sunscreen has an SPF from 2 to less than 4; "moderate" means the sunscreen has an SPF from 4 to less than 8; "high" means the sunscreen has an SPF from 8 to less than 12; "very high" means the sunscreen has an SPF from 12 to less than 20; and "ultrahigh" means the sunscreen has an SPF of from 20 to 30.

In reality, many people who are out in the sun have wet skin prior to their applying any sunscreen agent. Such people are often engaged in activities associated with a proximity to water, such as swimming, boating, or fishing which are conducive to their skin becoming wet. Attentively, people who are out in the hot sun, or are engaged in strenuous outdoor activities, such as sports, are prone to sweating, which also causes their skin to become wet.

The application of a sunscreen to wet skin, even those sunscreens which are "water resistant" or "waterproof" is contrary to their instructions for use and prevents them from having the efficacy which they proclaim to have when applied properly to dry skin and allowed to dry for the requisite time prior to the person being exposed to the sun.

In view of the foregoing, a new class of sunscreens, i.e., sunscreens which can be applied directly to wet skin, is needed. In addition, cosmetics, such as makeup, can be formulated to include the instant protection and "wet-appliable" benefits of the present invention. Finally, procedures for testing such "wet-appliable" sunscreens for efficacy are also needed.

As used herein, various trademarks and trade names are intended to refer to their chemical names as set forth in the following table:

| Trade Name | Material | CAS # |
|---|---|---|
| GANEX V220 | PVP/EICOSENE COPOLYMER | 28211-18-9 |
| POLYETHYLENE | POLYETHYLENE | 9002-88-4 |
| PVP/VA W735 | PVP/VA COPOLYMER | 25086-89-9 |
| PLANTAREN 2000 | DECYL GLUCOSIDE | 58846-77-8 |
| GERMABEN II | PROPYLENE GLYCOL (AND) | 57-55-6 |
|  | DIAZOLIDINYL UREA (AND) | 78491-02-8 |
|  | METHYLPARABEN (AND) | 99-76-3 |
|  | PROPYLPARABEN | 94-13-3 |
| DC 345 | CYCLOMETHICONE | 69430-24-6 |
| N-HANCE AG50 | C1–5 ALKYL GALACTOMANNAN |  |
| N-HANCE AG200 | C1–5 ALKYL GALACTOMANNAN |  |
| SF 1328 (NEW SF 1528) | CYCLOPENTASILOXANE (AND) | 69430-24-6 |
|  | DIMETHECONE COPOLYOL | 64365-23-7 |
| DC 345 | CYCLOMETHICONE | 69430-24-6 |
| ESCALOL 557 | OCTYL METHOXYCINNAMATE | 5466-77-3 |
| TRIVENT DIDA | DIISODECYL ADIPATE | 27178-16-1 |

-continued

| Trade Name | Material | CAS # |
|---|---|---|
| ARLACEL P135 | PEG-30 DIPOLYHYDROXY-STEARATE | 70142-34-6 |
| GANEX V220 | PVP/EICOSENE COPOLYMER | 28211-18-9 |
| CASTORWAX MP70 | HYDROGENATED CASTOR OIL | 8001-78-3 |
| Z-COTE | ZINC OXIDE | |
| GERMABEN II-E | PROPYLENE GLYCOL (AND) | 57-55-6 |
| | DIAZOLII)LNYL UREA (AND) | 78491-02-8 |
| | METHYLPARABEN (AND) | 99-76-3 |
| | PROPYLPARABEN | 94-13-3 |

SUMMARY OF THE INVENTION

In accordance with the present invention, a new class of "wet-appliable" sunscreens and makeup has been developed. These sunscreens can be applied to the wet skin of a user, yet they will, nevertheless, provide the user with the efficacy and SPF levels which are claimed. In addition, whether applied to wet or dry skin, the sunscreens of the present invention are immediately effective to provide protection to their PCD upon application, so no waiting time is required before the user can go into the sun or engage in activities in which their skin will become wet.

In addition, new procedures have been invented which are, for the first time, capable of being used to test the effectiveness of sunscreens with respect to how quickly they become effective and their ability to be applied while wet, while remaining effective.

DETAILED DESCRIPTION OF AN EXEMPLARY EMBODIMENT

Practically all sunscreen products sold in the United States are emulsions and virtually all of them are of the oil-in-water type. While water-in-oil sunscreen emulsions are well known, they have not enjoyed popularity due to their greasiness. Recent advances in technology have allowed for greatly improved versions of water-in-oil sunscreens. Nevertheless, oil-in-water sunscreens predominate by a vast margin. Unfortunately, these popular oil-in-water sunscreens are not inherently waterproof, so even the FDA requires that they be "reapplied" after swimming and/or perspiring. Reapplying an oil-in-water sunscreen emulsion results in smearing and uneven application of the sunscreen due to the fact that oil-in-water emulsions have water as their external phase. Thus, when an oil-in-water sunscreen emulsion is applied to wet skin the external (water) phase is diluted and the result is poor and uneven application. The present invention uses oil and silicones as the external phase, so no similar problems occur. The water-in-oil emulsion of the present invention is inherently waterproof since it contains a great predominance of lipophillic emulsifier. The result is a uniform and thick sunscreen film which remains on the skin, even when it is applied over wet skin. In fact one could even apply the sunscreen product of the present invention underwater.

In accordance with the present invention, a new class of "wet-appliable" sunscreens and makeup has been developed. These "wet-appliable" sunscreens and makeup are not only water resistant or waterproof, after they have been applied to the user, but they may be applied to a user whose skin is wet when they are applied.

In addition, the "wet-appliable" sunscreens and makeup of the present invention do not require any waiting time before they are effective to their designated SPF level. Consequently, the "wet -appliable" sunscreens and makeup of the present invention differ from the "water resistant" and "waterproof" sunscreens heretofore known in that they (1) may be applied to a person whose skin is wet; and (2) they are immediately effective when they applied, rather than after they have been first allowed to dry for a predetermined time.

The "wet-appliable" sunscreens and makeup of the present invention are based upon human skin being lipophilic, i.e., "oil loving", rather than hydrophilic, i.e., "water loving". That means that when the sunscreens of the prior art, which are typically oil-in-water emulsions, are applied to wet skin, they become milky and discontinuous. Accordingly, as the sunscreens of the prior art were intended to be applied to dry skin, then allowed to dry for a predetermined period of time (e.g., twenty minutes) prior to the user being exposed to the sun, it did not matter that they were oil-in-water emulsions. In reality, however, many people are not aware of the instructions which accompany sunscreens, or else they disregard these instructions. Consequently, they tend to apply sunscreens to their skins when they are wet, either from engaging in water activities, such as swimming, boating, and fishing, or from engaging in sports activities or when out in the hot sun, whereby their own sweat has wet their skin. In either case, when a sunscreen of the prior art is applied, the water on the user's skin prevents the sunscreen from drying properly to form a skin, which in the case of "water resistant" and "waterproof" sunscreens, would thereafter be protected from water, had it only been applied in accordance with its instructions. Lacking proper application the sunscreens of the prior art are unable to provide the protection which their labeling calls for, thereby leaving the user exposed to the very dangers which they thought they were avoiding by the application of the sunscreen.

In accordance with the present invention sunscreens and makeup are formulated with the specific intent that they can be applied to wet skin, i.e., a "wet-appliable" sunscreen, is described. Unlike the sunscreens of the prior art, which are oil-in-water emulsions, the "wet-appliable" sunscreens and makeup of the present invention are water-in-oil emulsions.

In particular, the preferred embodiment of the present invention makes use of a water-in-oil emulsifier containing at least one volatile emollient, and an oil soluble sunscreen. In specific embodiments of the invention, other constituents may also be present. In particular, it has been found that a "wet-appliable" sunscreen, which can be applied to a person having wet skin, or even to a person who is under water, can be formulated using the ingredients disclosed herein.

First, it has been discovered that if water is to be present in the sunscreen, then a water-in-oil emulsifier must be used. In accordance with the preferred embodiment of the present invention, a water-in-oil emulsifier, such as SF1328 is used in a percentage of between about 2–10%. SF1328 is a water-in-oil emulsifier supplied by GE Silicones. The chemical name for SF1328 is dimethicone (and) dimethicone copolyol. Other water-in-oil emulsifiers which could be used in place of SF1328 include Arlacel P135 (ICI, DC 3225C (Dow Coring), DC 5200, Abil EM-90, Abil WE-09 (Goldschmidt). Those skilled in the art will recognize that there are several other water-in-oil emulsifiers which could also be used in place of SF1328.

Next a volatile emollient, such as DC 345, which is a volatile emollient supplied by Dow Corning is used in a percentage of between about 5–20%. The chemical name of DC 345 is cyclomethicone. Those skilled in the art will again recognize that there are numerous other volatile emollients which could be used in lieu of DC 345, including low molecular weight dimethicones 0.65 cs–50 cs (Dow Corning) and Permethyls (hydrocarbons) supplied by Presperse Co.

An oil soluble sunscreen, such as Escalol 557, whose drug name is octyl methoxycinnamate, is used in a level of between about 2.0–7.5%. Any other Federal Food and Drug Administration (FDA) approved oil soluble UVB sunscreens can be used in the United States. Outside of the United States, any locally approved, oil soluble sunscreen could be used without departing from the present invention.

As set forth above, other substances may optionally be added to the "wet-appliable" sunscreen of the present invention in order to improve the ultimate formulation. These other substances include siliconyl beeswax, which is preferably used to a level between about 0.25–5.0%, and which is supplied by Koster Kuenen. The function of the siliconyl beeswax is to provide emulsion stabilization and waterproofing. Additionally it thickens the emulsion. Other materials which would accomplish these purposes, and which could, therefore, be used in lieu of the siliconyl beeswax, include polyethylene hydrogenated castor oil, beeswax, silica, alkyl modified silicones, mineral waxes, and/or vegetable waxes.

A non-volatile emollient ester is also used in the preferred embodiment of the invention. In the preferred embodiment, the non-volatile emollient ester which is used is called Trivent DIDA, whose chemical name is diisodecyl adipate, and which is supplied by Trivent Chemical Co., is used to a level of about 2–10%. Those skilled in the art will recognize that many other non-volatile emollient esters, or other lipophiles, could be used in place of Trivent DIDA.

In the preferred embodiment of the invention a number of other substances are included in the formulation. These include Arlacel P135, whose chemical name is PEG-30 dipolyhydroxystearate is a secondary water-in-oil emulsifier which is supplied by ICI. The purpose of the Arlacel P135 is to stearically stabilize the water-in-oil emulsion. The Arlacel P135 may be replaced by any typically employed water-in-oil emulsifier. As will be understood by those skilled in the art, the purpose of having a secondary water-in-oil emulsifier (which is present in a lower concentration than the primary water-in-oil emulsifier) is to provide a more stable emulsion.

The preferred embodiment of the invention also includes Ganex V220, which is also known as 2-pyrrolidinone, 1-ethenyl-, polymer with 1-eicosene, or poly (vinylpyrrolidone/1-eicosene which is a film thickener supplied by ISP Chemical Co. It functions as a film thickener, SPF booster, and as a waterproofing agent. As will be recognized by those skilled in the art, the Ganex V220 may be replaced by a number of other polymers that could function in similar manner, such as polyethylene, other PVP polymers, such as acetic acid ethenyl ester, polymer with 1-ethenyl-2-pyrrolidinone, or vinylpyrrolidone/vinyl acetate copolymer in water solution and acrylate resins.

The preferred embodiment of the invention also includes Fragrance MF-3871, which is a fragrance used for its organoleptic effect, i.e., it makes the formulation smell good. MF 3871, which is supplied by Mane USA, can be replaced by numerous other suitable oil soluble fragrances without departing from the present invention.

The preferred embodiment of the invention also includes Vitamin E Acetate, which is an antioxidant, and a free radical scavenger which is supplied by BASF Corporation. The purpose of the Vitamin E Acetate is to provide those benefits which are provided by antioxidents and free radical scavengers, although it is not needed for the present invention.

The preferred embodiment of the invention also includes Plantaren 2000, which is a hydrophilic surfactant which is supplied by Henkel Corporation. The purpose of the Plantaren 2000, which is used in level of between about 0.05% to 1.0% (by weight), is to stabilize the emulsion. The chemical name for Pantaren 2000 is lauryl polyglucose supplied by Henkel Corp. It functions as a hydrophilic surfactant to complex at the interface and provides a more uniform and stable interface, thereby stabilizing the emulsion. It is as a surfactant for shampoos and shower washes, rather than in the manner in which it is used in the present inventions. Many other hydrophilic emulsifers/surfactants could be used in place of the Plantaren 2000.

The preferred embodiment of the invention also includes Germaben II, which is a preservative, which is also known as 1,2-propanediol/vurea, N-[1,3-bis(hydroxymethyl)-2,5-diox-4imidazolidinyl]-N,N'-bis(hydroxymethyl)-/benzoic acid, 4-hydroxy-, methyl ester/benzoic acid, 4-hydroxy-, propyl ester, or propylene glycol and diazolidinyl urea and methylparaben and propylparaben which is supplied by Sutton Laboratories/ISP Corporation. The purpose of the Germaben II is to preserve the emulsion. The Germaben II, is preferably used in a level of between about 0.5% to about 1.5% by weight. It functions as a preservative. There are numerous other preservatives that could be used.

The preferred embodiment of the invention also includes sodium chloride. The purpose of the sodium chloride is to stabilize the water-in-oil emulsion. The sodium chloride may be replaced by magnesium sulfate or potassium chloride. Use levels of about 0.2–2.0%.

Finally, the preferred embodiment of the invention is formulated with deionized water, as an internal phase diluent as set forth more fully hereinafter.

The formulation of the preferred embodiment of the sunscreen of the present invention is as follows:

EXAMPLE 1

Sunscreen

| # | PHASE | INGREDIENT | % W/W | BATCH SIZE |
|---|---|---|---|---|
|  |  |  |  | 500.00 |
| 1 | A | SF 1328 EMULSIFIER | 8.00 | 40.00 |
| 2 | A | DC 345 CYCLOMETHICONE | 5.00 | 25.00 |
| 3 | A | ESCALOL 557 (SUNSCREEN) | 7.50 | 37.50 |
| 4 | A | TRIVENT DIDA | 5.00 | 25.00 |
| 5 | A | ESCALOL 567 (SUNSCREEN) | 4.00 | 20.00 |
| 6 | A | SILICONYL BEESWAX | 2.00 | 10.00 |

-continued

| # | PHASE | INGREDIENT | % W/W | BATCH SIZE |
|---|---|---|---|---|
| 7 | A | ARLACEL P135 | 1.00 | 5.00 |
| 8 | A | GANEX V220 | 2.00 | 10.00 |
| 9 | A | FRAGRANCE MF-3871 | 0.25 | 1.25 |
| 10 | A | VITAMIN E ACETATE | 0.50 | 2.50 |
| 11 | B | DEIONIZED WATER | 62.65 | 313.25 |
| 12 | B | PLANTAREN 2000 | 0.10 | 0.50 |
| 13 | B | SODIUM CHLORIDE | 1.00 | 5.00 |
| 14 | B | GERMABEN II | 1.00 | 5.00 |
|  |  | TOTAL | 100.00 | 500.00 |

In the foregoing formulation, SF1328 is the primary emulsifier. In accordance with the present invention, the primary emulsifier is present in a concentration of between about 2% to about 20% by weight, and it is preferably present in a concentration of between about 5% to about 10%.

The Arlacel P135 acts as the secondary emulsifier. In accordance with the present invention, the secondary emulsifier is present in a concentration of between about 0.25% to about 4% by weight, and it is preferably present in a concentration of between about 0.5% to about 1.5%. The secondary emulsifier helps to stabilize the formulation.

The Plantaren 2000 is a hydrophilic emulsifier which functions to stabilize the oil/water interface. In accordance with the present invention, the primary emulsifier is present in a concentration of between about 0.05% to about 0.5% by weight, and it is preferably present in a concentration of between about 0.05% to about 0.2%.

In order to manufacture the sunscreen of the Example 1, Phase A is heated to about 75° C. and it is mixed to uniformity.

Next, Phase B is combined and Phase B is added to Phase A very slowly under good agitation.

Finally, the combined Phases A and B are packaged.

EXAMPLE 2

Sunscreen

| # | PHASE | INGREDIENT | % W/W |
|---|---|---|---|
| 1 | A | DEIONIZED WATER | 34.30 |
| 2 | A | PROPYLENE GLYCOL | 2.00 |
| 3 | B | AVOBENZONE | 2.00 |
| 4 | B | OCTYL METHOXYCINNAMATE | 7.50 |
| 5 | B | OXYBENZONE | 6.00 |
| 6 | B | SF 1328 EMULSIFIER | 5.00 |
| 7 | C | WATER, DEIONIZED | 40.00 |
| 8 | C | CARBOMER | 0.20 |
| 9 | D | PEG-40 STEARATE | 0.30 |
| 10 | D | GANEX V220 | 2.00 |
| 11 | E | TRIETHANOLAMINE 99% | 0.20 |
| 12 | F | PRESERVATIVE | 0.50 |
|  |  | TOTAL | 100.00 |

To make the water-in-oil-in-water sunscreen emulsion formulation of Example 2, Phase A is heated to 75° C. Phase B is heated to 75° C., and Phase A is added to Phase B. Phase D is added to Phase C. Phase A/B is added to Phase C/D. Phase E is added and the combination is allowed to cool to 45° C., and then Phase F is added, to complete the formulation.

Sunscreen Ointment

While it has been discovered that a water-in-oil emulsifier must be used in order to make a wet appliable sunscreen in which the formulation contains water, as described above, if an ointment is desired, then there is no water in the formulation. So, in accordance with another embodiment of the invention, a sunscreen ointment which provides instant protection, but which does not contain water can be formulated with an oil soluble sunscreen as described in Example 3:

EXAMPLE 3

SPF 30 Sunscreen Ointment

| # | PHASE | INGREDIENT | % W/W |
|---|---|---|---|
| 1 | A | PETROLATUM | 71.10 |
| 2 | A | CARNUBA WAX | 1.00 |
| 3 | A | CERESIN WAX | 3.00 |
| 4 | A | SILCONYL BEESWAX | 2.00 |
| 5 | B | OCTOCRYLENE | 9.00 |
| 6 | B | OXYBENZONE | 6.00 |
| 7 | B | OCTYL METHOXYCINNAMATE | 7.50 |
| 8 | C | FRAGRANCE | 0.40 |
|  |  | TOTAL | 100.00 |

Example 3 is an SPF 30 ointment.

In order to manufacture the sunscreen ointment of Example 3, Phase A is heated to 85° C. and mixed to uniformity. Then, Phase B is combined and added to Phase A. The formulation is then mixed to uniformity and packaged.

Makeup

Makeup containing a sunscreen, which can be applied over wet skin, is also within the scope of the present invention. A formulation for such a makeup is described in Example 4:

EXAMPLE 4

Makeup with Sunscreen Protection

| # | PHASE | INGREDIENT | % W/W | BATCH SIZE |
|---|---|---|---|---|
|  |  |  |  | 500.00 |
| 1 | A | SF 1328 WATER IN OIL EMULSIFIER | 8.00 | 40.00 |
| 2 | A | CYCLOMETHICONE DC 345 | 5.00 | 25.00 |
| 3 | A | OCTYL STEARATE | 4.00 | 20.00 |
| 4 | A | ALUMINUM STEARATE | 2.00 | 10.00 |
| 5 | A | CASTORWAX MP70 | 1.25 | 6.25 |
| 6 | A | SILICONYL BEESWAX | 1.00 | 5.00 |
| 7 | A | OCTYL METHOXYCINNAMATE | 7.50 | 37.50 |
| 8 | A | OXYBENZONE | 2.00 | 10.00 |
| 9 | B | Z-COTE ZINC OXIDE | 3.00 | 15.00 |
| 10 | B | TITANIUM DIOXIDE # 328 | 15.00 | 75.00 |
| 11 | B | RED IRON OXIDE # 7067 | 0.50 | 2.50 |
| 12 | B | YELLOW IRON OXIDE # 7059 | 1.00 | 5.00 |
| 13 | B | BROWN IRON OXIDE # 7050 | 1.80 | 9.00 |
| 14 | B | BLACK IRON OXIDE # 7133 | 0.10 | 0.50 |
| 15 | C | DEIONIZED WATER | 46.15 | 230.75 |
| 16 | C | PLANTAREN 2000 | 0.10 | 0.50 |
| 17 | C | SODIUM CHLORIDE | 0.60 | 3.00 |

-continued

| # | PHASE | INGREDIENT | % W/W | BATCH SIZE |
|---|---|---|---|---|
| 18 | C | GERNABEB II | 1.00 | 5.00 |
| | | TOTAL | 100.00 | 500.00 |

In the foregoing makeup formulation, the SF1328 has a water in oil emulsifier.

In order to manufacture the makeup of Example 4, Phase A is heated about 80° C. Next, Phase B is added very slowly under moderate agitation. Next, Phase C is heated to 60° C., and added to the batch. Finally, the combined Phases A, B, and C are packaged.

The following three formulations also provide instant protection products that may be applied to wet skin. These formulations may make use of a new material, available from Hercules, called N'Hance AG 50 or AG200. These materials are alkyl galactomannan materials which act to thicken ointments, to create clear oil based gels, and to stabilize water-in-oil emulsions. Additionally, it will be understood by those skilled in the art that mention commonly utilized oil phase thickeners, such as polyvalent soaps (i.e., aluminum stearate, calcium stearate, magnesium stearate, or zinc stearate) or silica based materials (i.e., fumed silica Cab-O-Sil M5) can be used.

Sunscreen Gel

In one embodiment of the present invention, a gel based sunscreen is described. As gels do not include water, no water-in-oil emulsifier is required. A gel formulation is described in Example 5:

EXAMPLE 5

Sunscreen Gel SPF 15

A sunscreen gel having an SPF 15, which provides instant protection from the sun and which may be applied to wet skin to provide instant protection, is made as follows:

| # | PHASE | INGREDIENT | % W/W | BATCH SIZE |
|---|---|---|---|---|
| | | | | 500.00 |
| 1 | A | MINERAL OIL | 35.65 | 178.25 |
| 2 | A | DC 345 CYCLOMETHICONE | 33.00 | 165.00 |
| 3 | A | OCTYL METHOXYCINNAMATE | 7.50 | 37.50 |
| 4 | A | TRIVENT DIDA (DIISODECYL ADIPATE) | 5.00 | 25.00 |
| 5 | A | OXYBENZONE | 6.00 | 30.00 |
| 6 | A | N-HANCE AG200 | 5.00 | 25.00 |
| 7 | A | GANEX V220 | 2.00 | 10.00 |
| 8 | B | FRAGRANCE MF-3871 | 0.25 | 1.25 |
| 9 | B | VITAMIN E ACETATE | 0.50 | 2.50 |
| 10 | B | PROPYLPARABEN | 0.10 | 0.50 |
| 11 | B | OCTYLDODECANOL | 5.00 | 25.00 |
| | | TOTAL | 100.00 | 500.00 |

The sunscreen gel of Example 5 is manufactured by heating Phase A to about 85° C. and mixing to uniformity. Then Phase B is combined and added to Phase A. The mixture is mixed to informity and packaged.

In Example 6, another sunscreen ointment formulation is described:

EXAMPLE 6

Sunscreen Ointment having SPF 15

A sunscreen ointment having an SPF 15, which provides instant protection from the sun and which can be applied to wet skin is made, as follows:

| # | PHASE | INGREDIENT | % W/W | BATCH SIZE |
|---|---|---|---|---|
| | | | | 500.00 |
| 1 | A | MINERAL OIL | 27.65 | 138.25 |
| 2 | A | DC 345 CYCLOMETHICONE | 33.00 | 165.00 |
| 3 | A | OCTYL METHOXYCINNAMATE | 7.50 | 37.50 |
| 4 | A | PETROLATUM | 5.00 | 25.00 |
| 5 | A | TRIVENT DIDA (DIISODECYL ADIPATE) | 5.00 | 25.00 |
| 6 | A | CAB-O-SIL M5 FUMED SILICA | 3.00 | 15.00 |
| 7 | A | OXYBENZONE | 6.00 | 30.00 |
| 8 | A | ALUMINUM STEARATE | 5.00 | 25.00 |
| 9 | A | GANEX V220 | 2.00 | 10.00 |
| 10 | B | FRAGRANCE MF-3871 | 0.25 | 1.25 |
| 11 | B | VITAMIN E ACETATE | 0.50 | 2.50 |
| 12 | B | PROPYLPARABEN | 0.10 | 0.50 |
| 13 | B | OCTYLDODECANOL | 5.00 | 25.00 |
| | | TOTAL | 100.00 | 500.00 |

In order to manufacture the suncreen ointment of Example 6, Phase A is heated to 85° C. and mixed to uniformity. Then, Phase B is combined and added to Phase A. The formulation is then mixed to uniformity and packaged.

In Example 7, a sunscreen oil is described:

EXAMPLE 7

Sunscreen Oil having SPF 15

A sunscreen oil having an SPF 15, which provides instant protection from the sun and which can be applied to wet skin is made, as follows:

| # | PHASE | INGREDIENT | % W/W | BATCH SIZE |
|---|---|---|---|---|
| | | | | 500.00 |
| 1 | A | MINERAL OIL | 35.65 | 178.25 |
| 2 | A | DC 345 CYCLOMETHICONE | 33.00 | 165.00 |
| 3 | A | OCTYL METHOXYCINNAMATE | 7.50 | 37.50 |
| 4 | A | TRIVENT DIDA (DIISODECYL ADIPATE) | 5.00 | 25.00 |
| 5 | A | OXYBENZONE | 6.00 | 30.00 |
| 6 | A | N-HANCE AG200 | 5.00 | 25.00 |
| 7 | A | GANEX V220 | 2.00 | 10.00 |
| 8 | B | FRAGRANCE MF-3871 | 0.25 | 1.25 |
| 9 | B | VITAMIN E ACETATE | 0.50 | 2.50 |
| 10 | B | PROPYLPARABEN | 0.10 | 0.50 |
| 11 | B | OCTYLDODECANOL | 5.00 | 25.00 |
| | | TOTAL | 100.00 | 500.00 |

In order to manufacture the sunscreen oil of Example 7, Phase A is heated to 65° C. and mixed to uniformity. Then, Phase B is combined and added to Phase A. The formulation is then mixed to uniformity and packaged.

Testing Procedures

Prior to the present invention, there was no sunscreen available which claimed that it had either instant protection or the ability to be applied to a person whose skin was wet. As people tend to wait until they are out in the sun before they apply sunscreens, and as traditional sunscreens have always required application followed by drying time before they were effective, traditional sunscreens have been unable to provide the proper level of protection to people who went out into the sun and then applied sunscreen. In many cases, people would go out into the sun with the intention of staying for relatively brief periods, apply sunscreens, and not realize that they were not effectively protected to the rated SPF of the applied sunscreen. Thus, by way of example, someone who was concerned about sunburn, but unaware of the fact that traditional sunscreens failed to provide their rated SPF instantly, could have gone out into the sun, applied a sunscreen, and then removed themselves from the sun after a short time in an effort to limit their exposure. In such cases, the sunscreen may never have achieved the desired level of protection.

Similarly, when children are taken out to play at recess or during gym classes, if they were to apply traditional sunscreens, they would not have sufficient time to allow the sunscreens to dry prior to the time their outdoor exposure to the sun ended.

With respect to the other aspect of the formulations of the present invention, namely their ability to be effectively applied over wet skin, this is another very important quality of both sunscreens, which are often applied after bathing or sweating, and makeup, which is often applied to wet skin.

While the foregoing qualities of the present inventive formulations are quite important, heretofore there has been no way to quantify those qualities. Accordingly, in another aspect of the present invention, test procedures and methods have been invented to quantify the effectiveness of sunscreen formulations. These inventive test procedures can be used to determine the effectiveness of sunscreens which have been applied and which are either expected to be effective immediately or which are expected to have a particular SPF value.

In accordance with the present invention, a series of tests, unique to "wet-appliable" and "instant protection" sunscreens, has been developed. These sunscreen tests provide an inventive procedure for determining the efficacy of sunscreens, which have not been present in the "standard" test procedures heretofore used in connection with testing the sunscreens of the prior art.

The test procedures of the present invention are described as follows:

Test I (Standard Test Procedure)

The standard test procedure used for testing sunscreens is outlined in the FDA monograph of proposed rules for sunscreen testing which was published in the Federal Register, Vol. 43, No. 166, Aug. 25, 1978.

In accordance with the standard procedures for testing sunscreens, a light source, such as a Xenon Arc Solar Simulator (150 watts) is used as a source of ultraviolet light irradiation. Such devices, which provide a spectral output in the ultraviolet range which is comparable to that of natural sunlight, are described in detail in J. Invest. Dermatol. 53, 192 (1969), and they are available from Solar Light Company, Philadelphia, Pa.

In order to test the SPF, the following procedure is used. A Minimal Erythemal Dose ("MED") is defined as the time interval or dosage of UV light irradiation sufficient to produce a minimal perceptible erythema on untreated skin. Prior to the testing phase, the MED of each test subject is determined by a progressive sequence of timed UV light exposures, each of which is graduated incrementally by 25% over that of the previous site. Twenty-four hours after irradiation, the sites are evaluated for erythema according to the following scoring system:

| 0 | Negative, no visible reaction |
| +/– | Minimal erythema |
| 1+ | Defined erythema |
| 2+ | Moderate erythema |
| 3+ | Severe erythema |

Determination of SPF Values

A sufficient number of 5×10 cm test site areas are outlined with a surgical marking pen on the subject's back between the acapulae and the beltline, lateral to the midline. These areas are designated for the Test material(s) or Standard, with an adjacent site designated for a concurrent MED determination (unprotected control). The tests, as described below, are conducted. Then the Sun Protection Factor ("SPF") is determined. The SPF is defined to be:

$$SPF = \frac{MEDProtectedSkin}{MEDUnprotectedControlSite}$$

Test II (Sweat Procedure)

The intent of having a "sweat" test, is to be able to determine the effectiveness of a sunscreen which is applied to a person who has been sweating. Therefore, consistent with the procedure of the present invention, it is necessary to provide a panelist with conditions which are conducive to having them sweat, or, alternatively, to simulate their having been sweating. In accordance with the preferred embodiment of the present inventive test procedure a panelist enters the environmentally controlled "hotroom". The temperature, humidity and air movement are maintained at levels consistent with try (30) minutes of copious sweating, i.e., temperature of 95° F. to 105° F., relative humidity between 60% and 80%; and minimal air movement. The panelist then sits in the "hotroom" for thirty (30) minutes of copious sweating. The 30-minute test period begins when the subject starts to sweat profusely, with drops of sweat running down the test site. A 0.1 g portion of Test Material is then applied to the appropriate 5×10 cm test site and spread evenly over the site using a fingercot. This delivers a test film of 2 mg/cm$^2$.

A sunscreen product is applied and permitted to dry for 20 minutes. Following the drying period there follow four 20 minute immersions in a whirlpool. The SPF is then measured. While this "standard" test procedure is effective for testing the water resistance of the sunscreens of the prior art, it cannot be used to test "wet-appliable" sunscreens, as part of the test procedure involves allowing the sunscreen to dry for a twenty minute period.

The test product is then applied to the participants while they are in the hot room. A control product (8% Homosalate, SPF 4) is evaluated via the same protocol. Their SPFs were then measured. The Homosalate had an average measured SPF of 4.78 (SPF=3.71 to 5.85 with a 95% confidence level), while the sunscreen of the present invention had an average measured SPF of 18.54 (SPF=18.14 to 18.94 with a 95% confidence level).

This particular test illustrated the unexpected result that the SPF 15 sunscreen of the present invention had an increased SPF value when the sunscreen was applied to a wet subject.

As will be obvious to those skilled in the testing art, other procedures wherein panelists are engaged in sweat producing activities, such as exercise (i.e., walking on a treadmill), could be used to produce sweat on a test subject. Similarly, other acts, such as spraying a panelist with a saline solution which has been heated, as desired, to a known temperature can be used to simulate sweating. All such procedures are considered to be within the scope of the present invention, as its purpose is to simulate sweating.

Test III (Underwater Procedure)

Similar to the sweat test procedure of Test II, a test procedure to simulate a person applying sunscreen immediately after having been bathing is also within the scope of the present inventive testing procedures. Again, while a preferred embodiment is disclosed, it is considered to be within the scope of the present invention to wet a panelist by any appropriate means, including submerging them or spraying them. In the preferred embodiment of the procedure for testing the efficacy of a sunscreen on a person who had been bathing, panelists are submerged in a whirlpool, and while they are underwater the test product is applied. A control product (8% Homosalate, SPF 4) is evaluated via the same protocol. Their SPFs were then measured. The Homosalate had an average measured SPF of 4.40 (SPF=3.72 to 5.08 with a 95% confidence level), while the sunscreen of the present invention had an average measured SPF of 17.92 (SPF=15.89 to 19.95 with a 95% confidence level).

This particular test further illustrated the unexpected result that the protection provided by the SPF 15 sunscreen of the present invention actually increased when the sunscreen was applied to a subject who was under water.

Test IV (Mist Procedure)

The test sites on the panelists are misted with water. A 0.1 g portion of test material is applied to the moistened 5×10 cm test site and spread evenly over the site using a fingercot. This delivers a test film of 2 mg/cm$^2$. Immediately after test product application, the test site is divided into subsites which are used for a defined serial UV light exposure. A control product (8% Homosalate, SPF 4) is evaluated via the same protocol. Their SPFs were then measured. The Homosalate had an average measured SPF of 4.40 (SPF=3.72 to 5.08 with a 95% confidence level), while the sunscreen of the present invention had an average measured SPF of 18.66 (SPF=18.55 to 18.77 with a 95% confidence level).

This particular test again illustrated the unexpected result that the protection provided by the SPF 15 sunscreen of the present invention increased when the sunscreen was applied to a wet subject.

Test V (Instant Protection)

A sufficient number of test sites are outlined on the subject's back between the sapulae and the beltline, lateral to the midline, with a surgical marking pen. These areas are designated for the Test material(s) or Standard, with an adjacent site designated for a concurrent MED determination (unprotected control). A 0.1 ml or 0.1 g portion of Test material(s) or Standard, is applied to the appropriate 5×10 cm test site and spread evenly over the site using a fingercot. This delivers a test film of 2 mg/cm$^2$. Immediately after test product application, the test site is divided into subsites which are used for a defined serial UV light exposure. A control product (8% Homosalate, SPF 4) is evaluated via the same protocol. Their SPFs were then measured. The Homosalate had an average measured SPF of 5.26 (SPF=4.54 to 5.98 with a 95% confidence level), while the sunscreen of the present invention had an average measured SPF of 16.50 (SPF=13.95 to 19.05 with a 95% confidence level).

The sunscreens of the present invention provide instantaneous protection, as confirmed by the test procedure discussed herein. Those skilled in the art will recognize that compared to the standard FDA approved test, as set forth in the so-called "tentative final monograph", in which a waiting period (drying time) of 20 minutes following application of a sunscreen is used prior to testing, anything less than a 20 minute drying time to achieve fill SPF protection represents an improvement in protection to the user. Therefore, the intent of the present inventive test procedure is to substitute a time of less than 20 minutes, and preferably no time, between application and testing. Accordingly, it is considered to be within the scope of the present inventive test procedure to wait for less than 20 minutes between application and testing. In particular, any time of 10 minutes or less would be considered to be within the preferred range of waiting time.

Test VI (15 Minute Drying)

A sufficient number of test sites are outlined on the subject's back between the sapulae and the beltline, lateral to the midline, with a surgical marking pen. These areas are designated for the Test material(s) or Standard, with an adjacent site designated for a concurrent MED determination (unprotected control). A 0.1 ml or 0.1 g portion of Test material(s) or Standard, is applied to the appropriate 5×10 cm test site and spread evenly over the site using a fingercot. This delivers a test film of 2 mg/cm$^2$. At least 15 minutes after product application, the test site is divided into subsites which are used for a defined serial UV light exposure. A control product (8% Homosalate, SPF 4) is evaluated via the same protocol. Their SPFs were then measured. The Homosalate had an average measured SPF of 5.26 (SPF=4.54 to 5.98 with a 95% confidence level), while the sunscreen of the present invention had an average measured SPF of 17.26 (SPF=14.70 to 19.82 with a 95% confidence level).

I claim:

1. A wet appliable sunscreen, which may be applied to wet skin which provides instant, waterproof protection upon application, said sunscreen consisting of:
   (a) a primary water-in-oil emulsifier; and
   (b) at least one sunscreen selected from the group consisting of an oil soluble sunscreen and an inorganic sunscreen.

2. The wet appliable sunscreen of claim 1 further comprising at least one lipophillic emollient.

3. The wet appliable sunscreen of claim 2 wherein the lipophillic emollient is a volatile emollient.

4. The wet appliable suncreen of claim 3 wherein the primary water-in-oil emulsifier is selected from the group consisting of dimethicone and dimethicone copolyol.

5. The wet appliable sunscreen of claim 4 wherein the primary water-in-oil emulsifier is present by weight percentage of between 2% and 10%.

6. The wet appliable sunscreen of claim 4 wherein the primary water-in-oil emulsifier is present by weight percentage of about 8%.

7. The wet appliable sunscreen of claim 4 wherein the primary water-in-oil emulsifier is selected from the group consisting of SF 1328, Arlacel P135, DC 3225C, DC 5200, Abil EM-90, and Abil WE-09.

8. The wet appliable sunscreen of claim 3 wherein the volatile emollient is selected from the group consisting of cyclomethicone, low molecular weight dimethicones, and Permethyls.

9. The wet appliable sunscreen of claim 8 wherein the volatile emollient is present in a weight percentage of between about 5% and 20%.

10. The wet appliable sunscreen of claim 3 wherein the volatile emollient is present in a weight percentage of about 5%.

11. The wet appliable sunscreen of claim 3 wherein the oil soluble sunscreen is octyl methoxycinnamate.

12. The wet appliable sunscreen of claim 3, further comprising a substance to provide stabilization, thickening, and water resistance selected from the group consisting of siliconyl beeswax, polyethylene hydrogenated castor oil. beeswax, alkyl modified silicones, mineral waxes, and vegetable waxes.

13. The wet appliable sunscreen of claim 3, further comprising a non-volatile emollient ester.

14. The wet appliable sunscreen of claim 13, wherein said non-volatile emollient ester is diisodecyl adipate.

15. The wet appliable sunscreen of claim 3, further comprising a stabilizer.

16. The wet appliable sunscreen of claim 15 wherein said stabilizer is Arlacel P135.

17. The wet appliable sunscreen of claim 3, further comprising a film thickener.

18. The wet appliable sunscreen of claim 17 wherein said film thickener is selected from the group consisting of Ganex V220, polyethylene, PVP polymers, and acrylate resins.

19. The wet appliable sunscreen of claim 3, further comprising a fragrance.

20. The wet appliable sunscreen of claim 19 wherein said fragrance is MF-3871.

21. The wet appliable sunscreen of claim 3, further comprising an antioxidant.

22. The wet appliable sunscreen of claim 21 wherein said antioxidant is vitamin E acetate.

23. The wet appliable sunscreen of claim 3, further comprising a hydrophilic surfactant.

24. The wet appliable sunscreen of claim 23 wherein said hydrophilic suifactant is Plantaren 2000.

25. The wet appliable sunscreen of claim 3, further comprising a preservative.

26. The wet appliable sunscreen of claim 25 wherein said preservative is Germaben II.

27. The wet appliable sunscreen of claim 3, further comprising a salt.

28. The wet appliable sunscreen of claim 27 wherein said salt is selected from the group consisting of sodium chloride, magnesium sulfate, and potassium chloride.

29. The wet appliable sunscreen of claim 3 further comprising deionized water.

30. The sunscreen of claim 1 wherein the inorganic sunscreen is selected from the group consisting of titanium dioxide and zinc oxide.

31. A sunscreen ointment which can be applied to a wet human which provides instant protection consisting of:
   (a) petroleum jelly; and
   (b) an oil soluble sunscreen.

32. A sunscreen gel which can be applied to a wet human which provides instant protection consisting of:
   (a) mineral oil;
   (b) an emollient; and
   (c) an oil soluble sunscreen.

33. The sunscreen gel of claim 32 in which the emollient is cyclomethicone.

34. The sunscreen gel of claim 33 in which the oil soluble sunscreen is octyl methoxycinnamate.

35. A wet appliable sunscreen comprising:
   (a) about 8% SF 1328;
   (b) about 5% DC 345;
   (c) about 7.5% ESCALOL 557;
   (d) about 5% Trivent DIDA;
   (e) about 4% Escalol 567;
   (f) about 2% siliconyl beeswax;
   (g) about 1% Arlacel P135;
   (h) about 2% Ganex V220;
   (i) about 0.25% Fragrance MF-3871;
   (j) about 0.50% Vitamin E Acetate;
   (k) about 0.10% Plantaren 2000;
   (l) about 1% Sodium Chloride;
   (m) about 1% Germaben II; and
   (n) about 62.65% deionized water.

36. A method of providing instant sun protection of a predetermined SPF to a human, comprising:
   applying to said human a water-in-oil sunscreen emulsion consisting of:
     (a) a primary water-in-oil emulsifier;
     (b) at least one volatile emollient;
     (c) an oil soluble sunscreen;
     (d) an inorganic sunscreen selected fiom the group consisting of titanium dioxide and zinc oxide, whereby the full rated, predetermined SPF of said water-in-oil sunscreen emulsion is achieved upon application.

37. A method of providing sun protection of a predetermined SPF to a human having wet skin, comprising:
   applying to the wet skin of said human an oil soluble sunscreen, whereby the full rated, predetermined SPF of said oil soluble sunscreen is achieved.

38. The method of claim 37 in which said oil soluble sunscreen further comprises:
   (a) a primary water-in-oil emulsifier; and
   (b) at least one volatile emollient.

39. A method of providing instant sun protection of a predetermined SPF to a human, comprising:
   applying to the skin of said human an oil soluble sunscreen, whereby the full rated, predetermined SPF of said oil soluble sunscreen is instantly achieved upon application.

40. A makeup providing instant sunscreen protection which comprises:
   (a) about 8.00% SF 1328 without emulsifier;
   (b) about 5.00% cyclomethicone DC 345;
   (c) about 4.00% octyl stearate;
   (d) about 2.00% aluminum stearate;
   (e) about 1.25% Castorwax MP 70;
   (f) about 1.00% siliconyl beeswax;
   (g) about 7.50% octyl methoxycinnamate;
   (h) about 2.00% oxybenzone;

(i) about 3.00% Z-cote zinc oxide;
(j) about 15.00% titanium dioxide #328;
(k) about 0.50% red iron oxide #7067;
(l) about 1.00% yellow iron oxide #7059;
(m) about 1.80% brown iron oxide #7050;
(n) about 0.10% black iron oxide #7133;
(o) about 46.15% deionized water;
(p) about 0.10% Planteren 2000;
(q) about 0.60% sodium chloride; and
(r) about 1.00% Germaben IIE.

41. The sunscreen gel of claim 34 comprising:
(a) mineral oil in about 35.65 weight percent;
(b) DC 345 cyclomethicone in about 33.00 weight percent; and
(c) octyl methoxycinnamate in about 7.50 weight percent.

42. The sunscreen gel of claim 41 further comprising an alkyl galactomannan material.

43. The sunscreen gel of claim 42 wherein the alkyl galactomannan material is selected from the group consisting of N'Hance AG 50 and AG200.

44. The method of claim 39 in which said oil soluble sunscreen further comprises:
(a) a primary water-in-oil emulsifier; and
(b) at least one volatile emollient.

* * * * *